United States Patent [19]
Hossack et al.

[11] Patent Number: 5,891,037
[45] Date of Patent: Apr. 6, 1999

[54] ULTRASONIC DOPPLER IMAGING SYSTEM WITH FREQUENCY DEPENDENT FOCUS

[75] Inventors: John A. Hossack, Palo Alto; John W. Allison, Sunnyvale; Albert Gee, Los Altos, all of Calif.; Matthew O'Donnell, Ann Arbor, Mich.

[73] Assignee: Acuson Corporation, Mountian View, Calif.

[21] Appl. No.: 993,393

[22] Filed: Dec. 18, 1997

[51] Int. Cl.⁶ ........................................................ A61B 8/00
[52] U.S. Cl. ............................................ 600/453; 600/443
[58] Field of Search .................................. 600/442, 443, 600/454, 453, 459; 128/916

[56] References Cited

U.S. PATENT DOCUMENTS

| | | |
|---|---|---|
| 3,953,825 | 4/1976 | Kino et al. . |
| 4,016,750 | 4/1977 | Green . |
| 4,140,022 | 2/1979 | Maslak . |
| 4,395,913 | 8/1983 | Hassler . |
| 4,403,311 | 9/1983 | Tournois . |
| 4,403,314 | 9/1983 | Tournois . |
| 4,446,740 | 5/1984 | Wilson et al. . |
| 4,456,982 | 6/1984 | Tournois . |
| 4,458,342 | 7/1984 | Tournois . |
| 4,550,607 | 11/1985 | Maslak et al. . |
| 4,699,009 | 10/1987 | Maslak et al. . |
| 4,870,971 | 10/1989 | Russell et al. . |
| 4,974,558 | 12/1990 | Katakura et al. . |
| 5,014,712 | 5/1991 | O'Donnell . |
| 5,105,814 | 4/1992 | Drukarey et al. . |
| 5,113,706 | 5/1992 | Pittaro . |
| 5,142,649 | 8/1992 | O'Donnell . |
| 5,218,869 | 6/1993 | Pummer . |
| 5,228,007 | 7/1993 | Murakami et al. . |
| 5,235,982 | 8/1993 | O'Donnell . |
| 5,282,471 | 2/1994 | Sato ........................................ 600/443 |
| 5,285,788 | 2/1994 | Arenson et al. ........................ 600/442 |
| 5,301,674 | 4/1994 | Erikson et al. . |
| 5,322,068 | 6/1994 | Thiele et al. . |
| 5,325,858 | 7/1994 | Moriizumi ............................. 600/443 |
| 5,608,690 | 3/1997 | Hossack et al. . |
| 5,651,365 | 7/1997 | Hanafy et al. ......................... 600/459 |

OTHER PUBLICATIONS

P. Tournois; "Acoustical Imaging Via Coherent Reception of Spatially Coloured Transmission"; 1980 Ultrasonic Symposium; pp. 747–750.

"Synthesis of the driving functions of an array for propagating localized wave energy", J.E. Hernandez et al., J. Acoust. Soc. Am. 92 (1), Jul. 1992, pp. 550–562.

"Simulated Capillary Blood Flow Measurement Using a Nonlinear Ultrasonic Contrast Agent", B. Schrope et al., Ultrasonic Imaging 14, pp. 134–158 (1992).

IEEE Transactions on Ultrasonics, Ferroelectrics, and Frequency Control, vol. 37, No. 5, Sep. 1990, "Ultrasonic Nondiffracting Transducer for Medical Imaging", Jian–Yu Lu et al., pp. 438–447.

(List continued on next page.)

*Primary Examiner*—Marvin M. Lateef
*Assistant Examiner*—Maubin Patel
*Attorney, Agent, or Firm*—Brinks Hofer Gilson & Lione

[57] ABSTRACT

A method for measuring Doppler ultrasound information transmits a transmit beam having a frequency dependent focus in which low-frequency components of the transmit beam are focused at long ranges and progressively higher frequency components of the transmit beam are focused at progressively shorter ranges. Beamformed receive signals are generated in response to receive signals from the transducers, and these beamformed receive signals are applied to Doppler processors. The frequency dependent focus of the transmit beam provides a transmit beam that is more uniform in width and intensity, and the Doppler processors thereby provide an improved Doppler image signal.

26 Claims, 5 Drawing Sheets

OTHER PUBLICATIONS

IEEE Transactions on Ultrasonics, Ferroeletrics, and Frequency Control, vol. 39, No. 3, May 1992, "Experimental Verification of Nondiffracting X Waves", Jian–yu Lu et al., pp. 441–446.

IEEE Transactions on Ultrasonics, Ferroelectrics, and Frequency Control, vol. 39, No. 1, Jan. 1992, "Non–diffracting X Waves–Exact Solutions to Free–Space Scalar Wave Equation and Their Finite Aperture Realizations", Jian–yu Lu et al., pp. 19–31.

Synchronous Dynamic Focusing for Ultrasound Imaging; G. Manes, et al.; IEEE Transactions on Ultrasonics, Ferroelectrics, and Frequency Control, vol. 35, No. 1, Jan. 1988; pp. 14–21.

Properties of Swept FM Waveforms in Medical Ultrasound Imaging; C.R. Cole; 1991 Ultrasonics Symposium, pp. 1243–1248.

Frequency Synthesis by Phase Lock; William F. Egan, Ph.D., Senior Engineering Specialist GTE Products Corporation; Lecturer in Electrical Engineering University of Santa Clara, Robert E. Krieger Publishing Company, Malabar, Florida 1990; pp. 14–29.

Stanford Research Systems; Synthesized Function Generator; Model DS345–30 MHz Function & Arbitrary Waveform Generator; 1994; pp. 8–13.

Stanford Research Systems; Scientific and Engineering Instruments 1994–1995; pp. 171–176.

"New Beamforming approach using high bandwidth transducers," J.A. Hossack, SPIE 'Medical Imaging' Conference, Paper 3037–16, 28th Feb. 1997.

5,891,037

ULTRASONIC DOPPLER IMAGING SYSTEM WITH FREQUENCY DEPENDENT FOCUS

BACKGROUND OF THE INVENTION

This invention relates to an ultrasonic Doppler imaging apparatus and method that utilize a different type of transmit signal to enhance the resulting Doppler image.

Color Doppler imaging is a known ultrasonic imaging mode that is particularly used in medical imaging applications. In color Doppler imaging, a transmit signal is applied to a transducer array to create ultrasonic beams in the tissue of interest. Ultrasonic echoes resulting from these beams are received by the transducer array and converted to receive signals that are beamformed and then applied to a color Doppler processor. The color Doppler processor can use autocorrelation techniques to estimate various Doppler parameters such as energy, variance and velocity for Doppler shifted echo signals associated with moving targets. Another type of motion processor performs frame-to-frame correlations to determine direction and magnitude of scatterer motion. Typically, the resulting Doppler parameters are displayed using a color display, in which differing levels of Doppler energy, variance or velocity are color-coded. For example, Doppler ultrasonic imaging can be used to diagnose blood velocity in cardiac imaging applications.

Another type of Doppler imaging is termed Doppler tissue imaging, and is described for example in Arenson, et al. U.S. Pat. No. 5,285,788, assigned to the assignee of this invention. In this imaging mode, low pass filters and clutter filters are reduced or eliminated to provide Doppler images of slowly moving or stationary tissue.

All of these Doppler imaging modes suffer from the disadvantage that conventional transmit pulses result in a transmit beam that varies in width with depth or range. Such depth-dependent variations can represent an important limitation, because the signal-to-noise ratio of the resulting echo signal will vary substantially as a function of depth. Since the transmit beam is not optimally uniform in width, the use of multiple receive beams for a single transmit beam may be limited due to non-uniformity of insonification intensity and beam width as a function of depth near the edge of the receive beams.

The present invention is directed to an improved ultrasonic Doppler imaging system that reduces or overcomes these problems of the prior art.

SUMMARY OF THE INVENTION

The present invention is defined by the following claims, and nothing in this section should be taken as a limitation on those claims.

By way of introduction, the ultrasonic imaging system disclosed below transmits ultrasonic energy using a plurality of transducers. Each transducer is responsive to a respective transmit waveform to produce a respective transducer waveform. The transmit waveforms each include multiple frequency components included in a single burst of energy. Lower frequency components are timed to cause corresponding lower frequency components of the transducer waveforms to focus at a greater depth, and progressively higher frequency components are timed to cause corresponding higher frequency components of the transducer waveforms to focus at progressively lesser depths. This type of transmit waveform provides a transmit beam that is more uniform in beam width and beam intensity as a function of depth.

The system described below generates beamformed receive signals in response to the receive signals from the transducers, and then Doppler processes the beamformed receive signals. Because the transmit beam is more uniform in beam width and beam intensity as a function of depth, the signal-to-noise ratio of the beamformed receive signals will be more uniform as a function of depth. This allows multiple receive beams to be acquired with greater confidence from a single transmit beam, since the receive beams situated near the edge of the transmit beam suffer less distortion. The frame rate and therefore the temporal resolution of the Doppler images can be improved, since wider transmit beams and fewer of them can be used if so desired.

DETAILED DESCRIPTION OF THE PRESENTLY PREFERRED EMBODIMENTS

Figure 1:
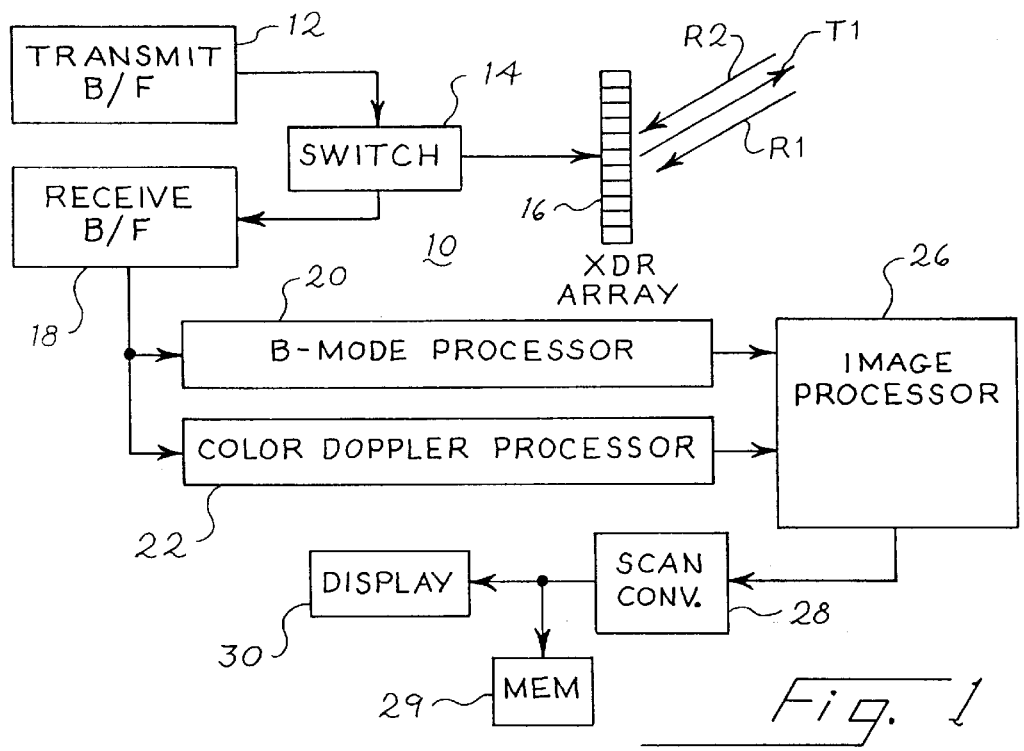
FIG. 1 is a block diagram of a ultrasonic imaging system that incorporates a presently preferred embodiment of this invention.

FIG. 1 shows an ultrasonic imaging system 10 that includes a transmit beamformer 12 that applies transmit waveforms via a switch 14 to individual transducers 16 included in a transducer array, such as a linear phased array. The transmit waveforms are timed and phased such that the transducers 16 form transducer waveforms that insonify the region of interest and coherently add along a transmit scan line T1. Ultrasonic echoes from the region of interest travel back to the transducers 16 of the transducer array, and the transducers 16 form electrical receive signals in response to these ultrasonic echoes. These receive signals are transmitted via the switch 14 to a receive beamformer 18. The receive beamformer 18 coherently adds receive signals from the transducers 16 to form beamformed signals for a succession of points along one or more receive scan lines R1, R2. In the simplest case, there is only a single receive scan line R1 for each transmit scan line T1, and the scan lines R1, T1 are superimposed. In more complex, multiple receive beam applications, two or more receive scan lines R1, R2 are formed from echoes associated with a single transmit event. This single transmit event can result in one or more transmit scan lines T1, and the multiple receive scan lines R1, R2 may be offset in azimuth with respect to the respective transmit scan line T1. In FIG. 1, two receive scan lines R1, R2 are shown offset by an azimuthal angle on either side of the transmit scan line T1.

The beamformed image signals generated by the receive beamformer 18 are applied to selected ones of a B-mode processor 20 and a color Doppler processor 22. The B-mode processor 20 generates image signals having an intensity related to the intensity of the beamformed signal from a corresponding portion of the imaged region. The color Doppler processor 22 generates image signals which vary according to selected Doppler parameters of the beamformed signal supplied by the receive beamformer 18.

Image signals generated by the processors 20, 22 are applied via a conventional image processor 26 and scan converter 28 to a display 30. A memory 29 can be used to store frames of image data for later analysis.

Figure 2:
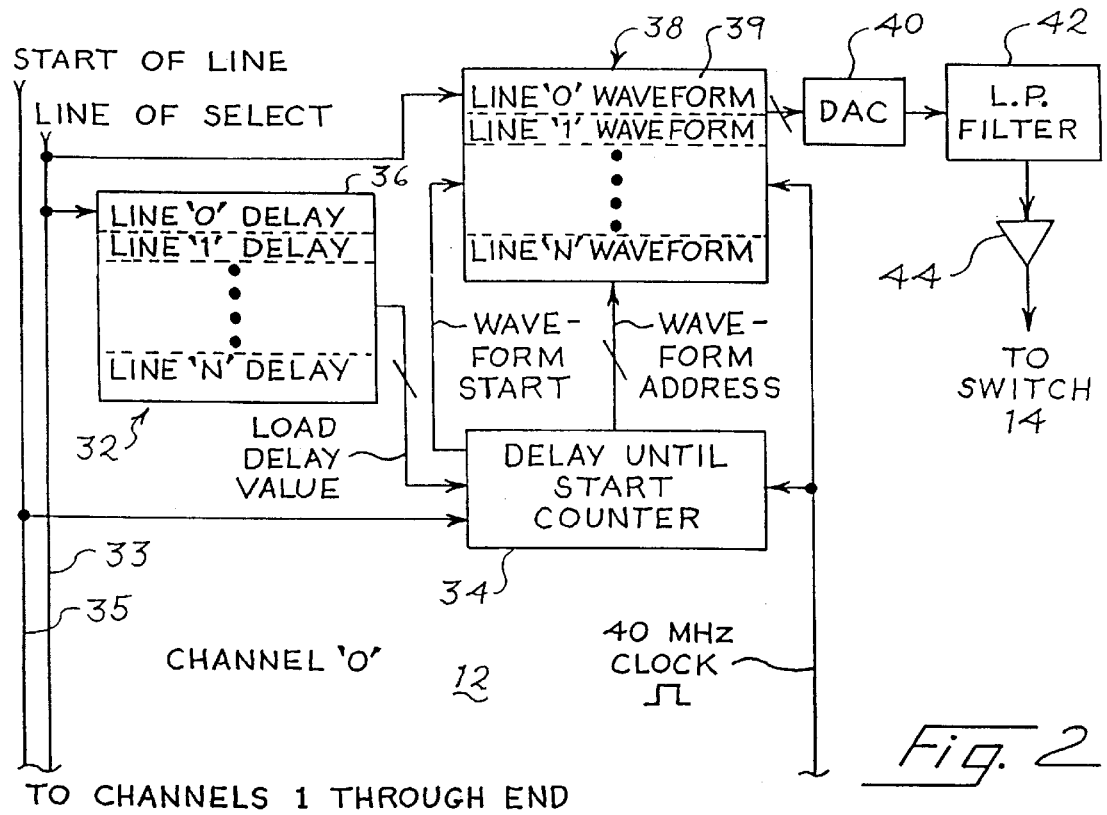
FIG. 2 is a block diagram of the transmit beamformer of FIG. 1.

The transmit beamformer 12 of FIG. 1, as shown in greater detail in FIG. 2, includes N channels, one for each of the transducers 16 (FIG. 1). Each channel includes a delay memory 32, a waveform memory 38, and a delay counter 34 (FIG. 2). The delay memory 32 includes 256 words 36, one for each possible steering angle or ultrasound scan line. The waveform memory 38 includes 256 sections 39, one for each possible steering angle. Each word 36 is set equal to a negative number equal to the number of clock cycles that elapse between a start-of-line signal and the first non-zero value of the associated waveform. For simplicity, it is assumed that zero is defined as a word having the most significant bit equal to 1 and all other bits equal to 0. Hence, the most significant bit becomes an enable signal for the memory. Each section 39 stores a respective waveform, for example as 64 or 128 successive eight bit words. When a section 39 is read with a 40 MHz clock, the resulting sequence of digital values defines a waveform approximately 1.6 to 3.2 micro-second in duration. The delay memory 32 is not required, but it reduces memory requirements for the waveform memory 38. This is because the delay memory 32 eliminates the need to store a large number of leading zeros when the ultrasound line is steered at a large angle.

In use, each channel responds to a scan line selection signal on line 33 by loading the word 36 for the selected scan line into the delay counter 34, and by enabling the selected section 39 of the waveform memory 38. Typically, each word 36 stores a negative binary integer equal to the desired delay before the first non-zero value of the respective waveform.

The delay counter 34 responds to a start of scan line signal on line 35 by incrementing the stored value with each cycle of a 40 MHz clock. When the counter 34 increments to zero, it enables the waveform memory 38. Subsequently generated values of the counter 34 (incrementing now from zero upwards) become address values for the memory 38. As each word of the section 39 for the selected scan line is addressed, the corresponding eight bit word is read and applied to a digital-to-analog converter 40. The analog output signal of the converter 40 is passed through a low-pass filter such as a Bessel filter 42 to reduce sampling effects and then to an amplifier 44. The output of the amplifier 44 is the transmit waveform discussed above that is applied to the respective transducer 16 via the multichannel switch 14 (FIG. 1).

Figure 3:
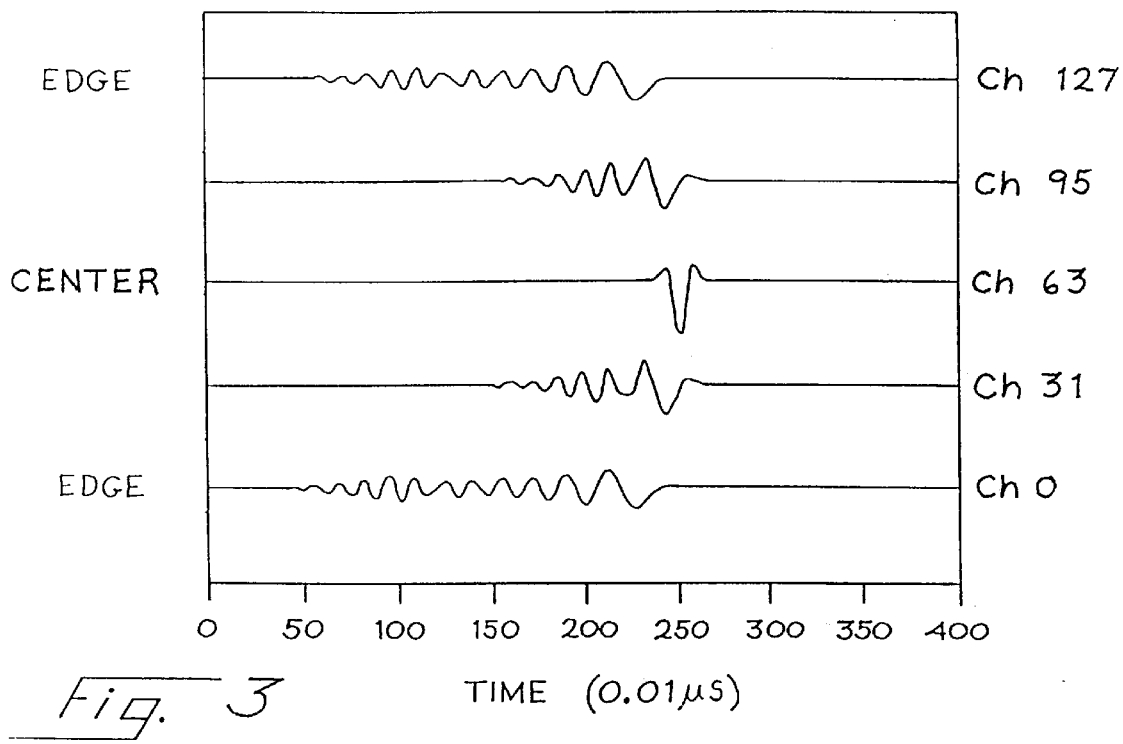
FIGS. 3 through 5 are diagrams illustrating frequency and focusing characteristics of transmit waveforms generated by the transmit beamformer of FIG. 2.
Figure 4:
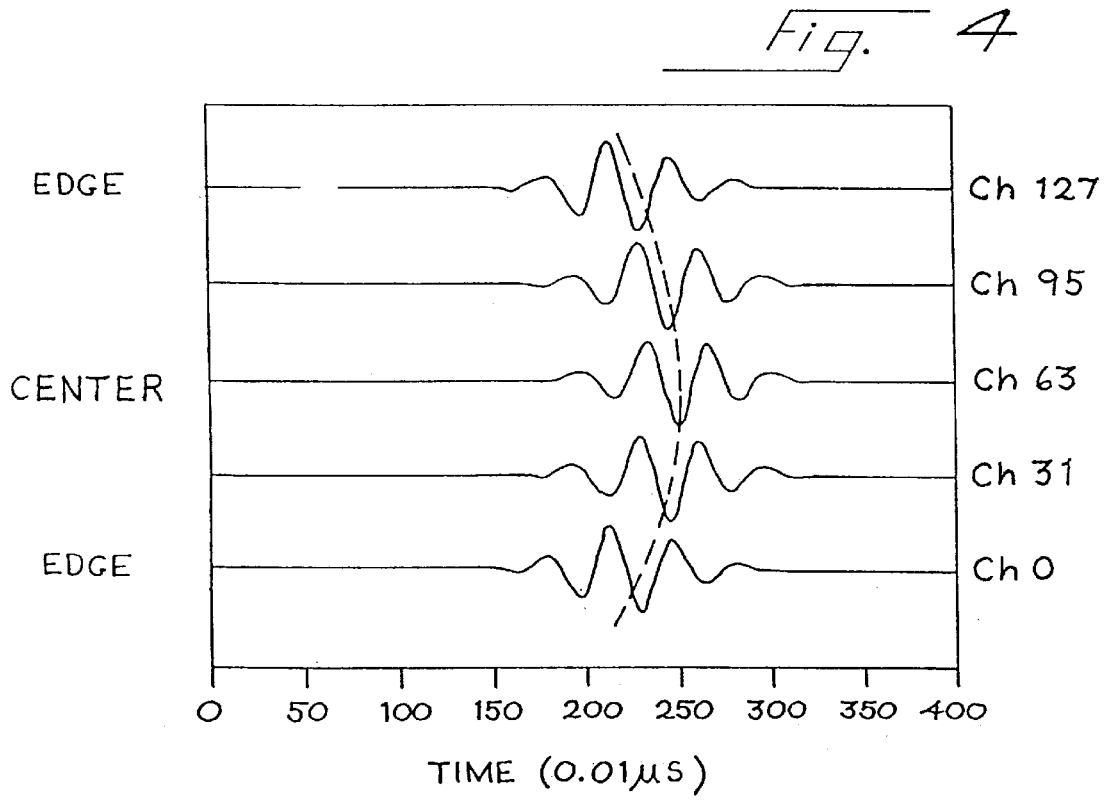
Figure 5:
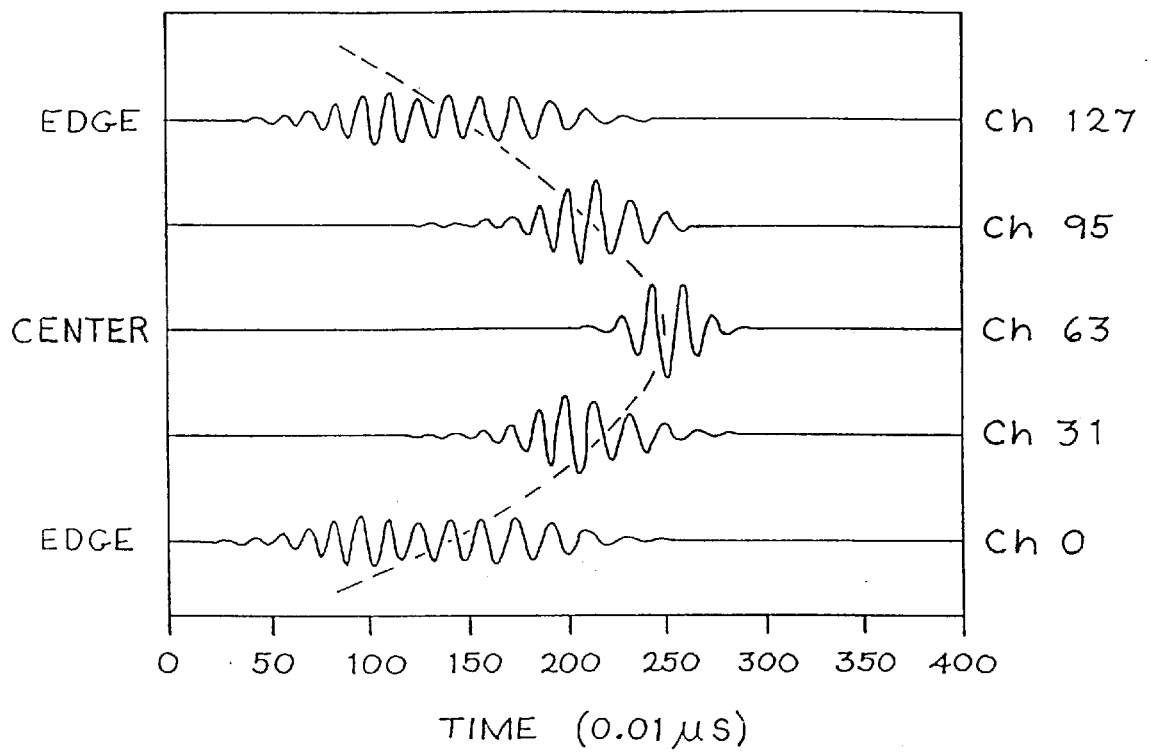

FIG. 3 shows the transmit waveforms for five of the transducers Ch0, Ch31, Ch63, Ch95, Ch127, where Ch0 and Ch127 are the transmit waveforms for the end transducers, and Ch63 is the transmit waveform for one of the two central transducers. Note that in each case all of the frequency components in any one transmit waveform are combined in a single burst of energy or a single frequency modulated pulse signal, rather than a sequence of multiple unmodulated pulses. Each transmit waveform is a continuously, constantly varying signal, rather than multiple pulses separated by a non-varying period lasting more than two times the period of the lowest frequency within the −6 dB bandwidth of the transmit waveform. FIG. 4 shows the transmit waveforms of FIG. 3 filtered with a bandpass filter centered at 3 MHz. The dotted line in FIG. 4 shows the curved wavefront of the 3 MHz components, that causes these lower frequency components to focus at the long range of 70 mm. FIG. 5 shows the transmit waveforms of FIG. 3 filtered with a bandpass filter centered at 7 MHz. The dotted line in FIG. 5 shows the more deeply curved wavefront of 7 MHz components, that causes these higher frequency components to focus at the short range of 40 mm.

Note that the transmit waveform for each transducer includes a wide range of frequency components, and the delays for individual frequency components are selected such that the separate frequency components of each transmit waveform are focused at respective focal ranges. The transducer waveforms produced by the transducer array as a whole generate a continuous line focus rather than a point focus, and differing frequency components are focused at differing ranges or depths along the line. At least for some of the transmit waveforms, the various frequency components are contained in a single burst of energy.

Thus, the transmit waveforms provided by the transmit beamformer 12 cause the transducers 16 to focus ultrasonic energy at selected frequencies at corresponding selected depths in the imaged region. Because individual frequency components have been delayed and phased to focus properly at the selected depths, the resulting transmit beam can be made relatively uniform in width as a function of depth. Further information regarding design of the transmit waveforms of FIG. 3 and the transmit beamformer of FIG. 2 can be found in Hossack et al., U.S. Pat. No. 5,608,690, assigned to the assignee of the present invention, which is hereby incorporated by reference in its entirety.

Figure 6:
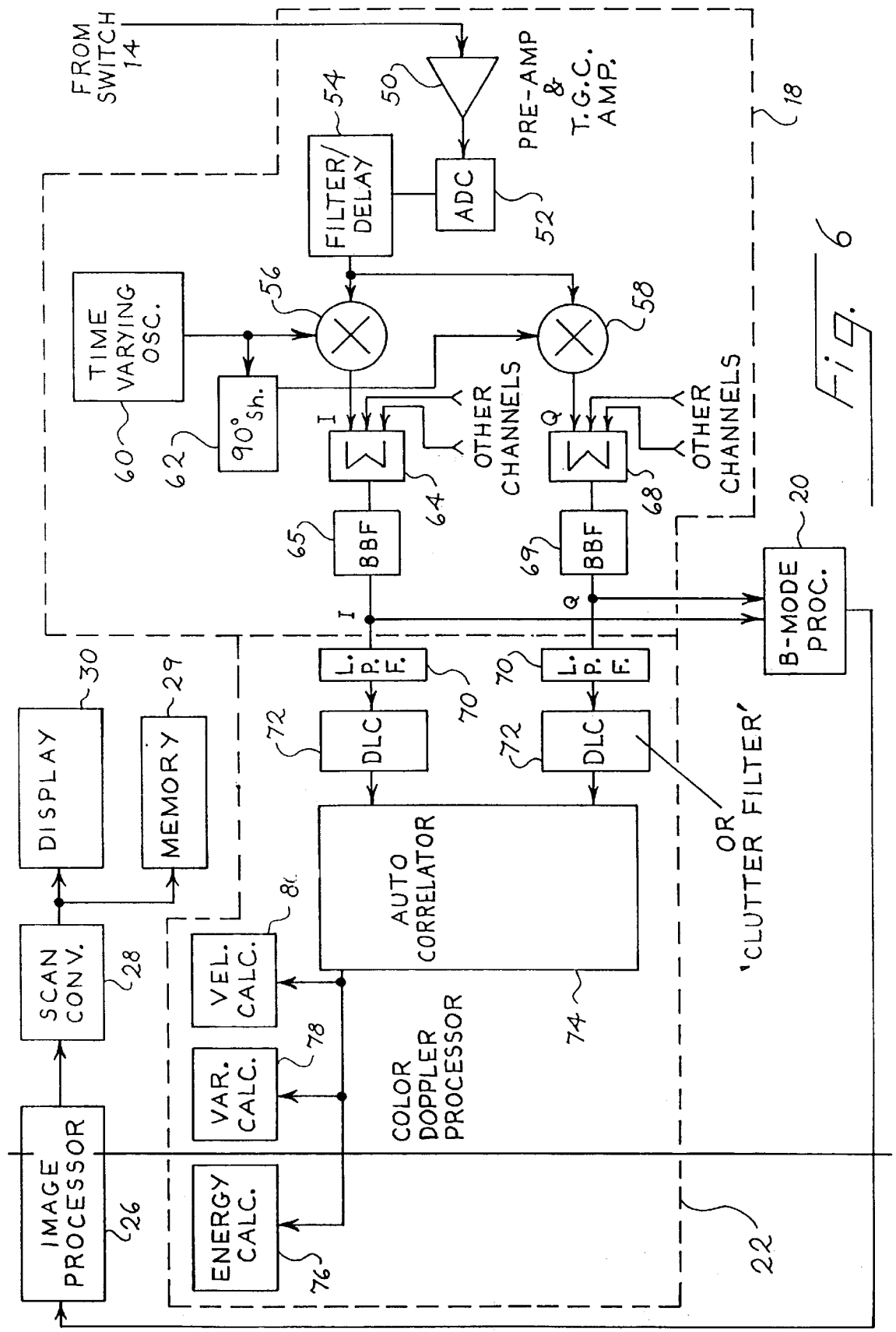
FIG. 6 is a block diagram of elements of the imaging system of FIG. 1 downstream of the switch 14.

FIG. 6 provides a block diagram of remaining components of the system 10 of FIG. 1, downstream of the switch 14. As shown in FIG. 6, the receive beamformer 18 includes a preamplifier 50 that amplifies the receive signal from the switch 14 and applies the amplified signal to an analog-to-digital converter 52. The digitized signal generated by the converter 52 is applied to a filter/delay unit 54 that applies appropriate focusing delays and/or phase rotations. Filtered and delayed digitized values are then demodulated using multipliers 56, 58. The multipliers 56, 58 also receive demodulation signals generated by a time-varying oscillator 60. In the case of the multiplier 58, the demodulation signal is phase-shifted by 90° by the phase shifter 62. The frequency of the time-varying demodulation frequency is adjusted dynamically as a function of time during processing of a single receive beam to insure that the frequencies which are ideally focused at the range of interest are properly centered at baseband (0 Hz). The time-varying demodulation waveform may be derived by any one of a number of digital synthesizer techniques. See, for example, K. F. Egan, "Frequency Synthesis By Phase Lock", Krieger, 1990. The demodulator including the multipliers 56, 58 and the time varying oscillator 60 functions as a time-varying filter that processes receive signals from the transducers. The system control signal that controls the frequency of the time-varying demodulation frequency may also be supplied to the B-mode processor 20 and the color Doppler processor 22. This control signal may be used by the B-mode processor to vary gains and/or filter parameters to obtain a more uniform image, and by the color Doppler processor 22 as described below to determine Doppler velocity.

I and Q demodulated receive signals supplied as outputs by the multipliers 56, 58 are summed in summers 64, 68 with corresponding signals from other channels associated with other transducers. The output of the summers 64, 68 are I, Q beamformed signals supplied at the output of the receive beamformer 18.

Baseband filters 65, 69 process the beamformed I, Q signals so that only the well-focused portion of the available signal energy in a frequency range around 0 Hz proceeds to the Doppler processor 22.

The variation of demodulation frequency as a function of depth (and therefore time) may take into account the variation of frequency as a function of focal depth used for the transmit waveforms described above. The variation of demodulation frequency as a function of depth may also take into account the observed reduction in center frequency due to frequency-dependent tissue-related attenuation. The optimal values for demodulation frequency as a function of depth or time may be arrived at by modeling the operation of the beamformer 18 and Doppler processor 22, taking into account assumed attenuation effects, or by experimental analysis.

With reference to FIG. 6, the beamformed I, Q signals are applied in parallel to the B-mode processor 20 and the color Doppler processor 22. Once the baseband, beamformed signal is filtered, Doppler processing is performed on the I and Q beamformed signals to derive Doppler related frequency shifts resulting from blood flow. Doppler processing is well-known in the art. See for example "Real Time Two-Dimensional Blood Flow Imaging Using an Autocorrelation Technique", Kasai, et al. Trans. Son. and Ultrason. Volume SU-32, pages 458–464, 1985. See also the detailed discussion in Maslak, U.S. Pat. No. 5,555,534, also assigned to the assignee of this invention.

The color Doppler processor 22 includes low-pass filters 70, clutter filters 72 and an autocorrelator 74. The clutter filters 72 are typically formed as delay line cancellers, and they are used as low-frequency rejection filters to eliminate large echo signals from stationary and slow moving objects which have a low or zero Doppler frequency shift. The autocorrelator 74 autocorrelates input signals from the clutter filters 72 and produces output signals for a Doppler energy calculator 76, a Doppler variance calculator 78 and a Doppler velocity calculator 80. The integration time of the autocorrelator 74 may be made variable depending upon the diagnostic application. The calculators, 76, 78, 80 operate in the conventional manner to apply respective Doppler parameter output signals to the image processor 26. The image processor 26 processes the output signals from the calculators 76, 78, 80 and combines them in any desired combination prior to providing them to the scan converter 28. Typically, images associated with the color Doppler processor are color-coded so that the user can identify the location and the speed or energy of blood flow within a B-mode image which is used for reference purposes.

In practice, separate excitation events are generally used for B-mode and color Doppler imaging. On occasion, a lower ultrasonic frequency is used for color Doppler imaging when penetration and a lack of aliasing are more important than spatial resolution in color Doppler processing.

The bandwidth requirements for B-mode processing and color Doppler processing are different, and therefore, optional filters are used in the input stages for both the color Doppler processor 22 and the B-mode processor 20. Preferably, these filters are complex digital FIR filters having time-varying coefficients, though other, simpler types of filters may be used, and may be preferred in some applications for reasons of cost.

The Doppler shift frequency determined by the autocorrelator 74 is a function of the center operating frequency pursuant to the following equation:

$$Fd = Fo \cdot c \cdot \cos(\theta)/(2 \cdot Vd), \text{ where} \qquad \text{(Eq 1)}$$

Fd=the Doppler shifted frequency,

Fo=the instantaneous transmitted center frequency (which is typically a function of depth and time), c=the speed of sound in tissue, θ=the angle of beam incidence with respect to flow of direction, and Vd=the velocity of the target such as blood scatterers.

The value of the velocity of the target, Vd, can be derived from Eq 1 as follows:

$$Vd = Fd \cdot c/(2 \cdot Fo \cdot \cos(\theta)). \qquad \text{(Eq 2)}$$

Since Fo is a function of range as discussed above, it is preferred to use a time-varying mapping function for relating an observed value of the Doppler shifted frequency Fd to a current estimate of the velocity of the target Vd. This ensures that the velocity of the target Vd which is displayed as a colored region superimposed on a B-mode gray scale image is accurate. The preferred mapping function is determined from the function of transmitted center frequency Fo versus range or time. The angle θ in Eq 2 is typically derived from information supplied by the user via a conventional graphical interface. For example, the user can manually input a line indicating the known direction of flow in the color region of interest, and the system can then calculate the angle θ between the user-supplied direction of flow and the beam direction. The system can apply cos (θ) in Eq 2 above, as is conventional in the art.

As shown in FIG. 6, any desired combination of Doppler parameters including energy, variance and velocity can advantageously be formed using the frequency dependent transmit focus described above. The greater uniformity of transmit intensity as a function of range may make Doppler power or Doppler energy imaging more uniform in terms of display resolution and sensitivity. This can represent an improvement with respect to conventional Doppler imaging systems, where performance is optimized in the region of the selected transmit focus and is inferior at points distant from this focus.

Figure 7:
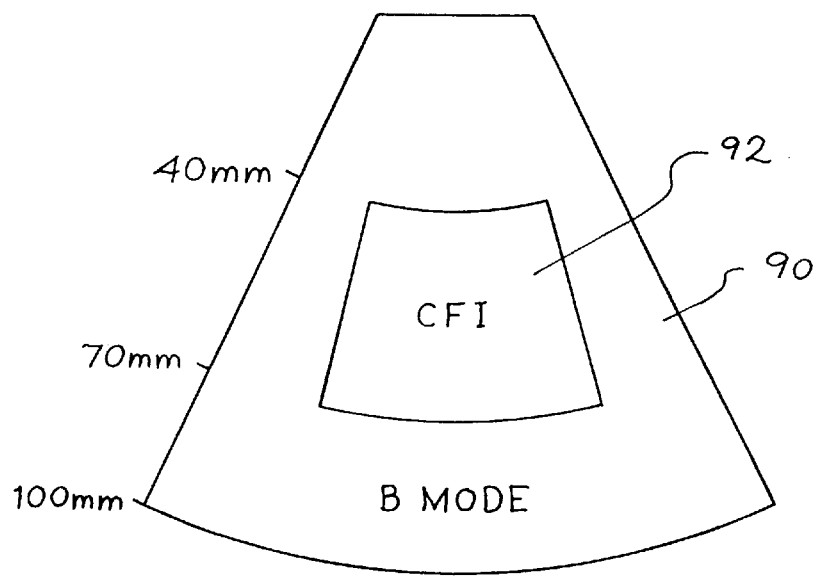
FIG. 7 is a schematic diagram of a Doppler image generated by the system of FIG. 1.

As shown in FIG. 7, the system 10 can be used to form a composite image including a B-mode portion 90, and a color Doppler portion 92. In the example of FIG. 7, the color Doppler portion 92 is confined to a color pan box between the ranges of 40 mm and 70 mm. Within the user-selected Doppler portion 92, the transmit beamformer 12 is used to provide broadband transmit pulses having higher frequencies focused toward the shallow end and lower frequencies focused toward points at the deeper end. It is not necessary to have the focal depths extend over the full dimensions of the Doppler portion 92. Also, it is not necessary to use any more than a fraction of the available transducer bandwidth.

Figure 8:
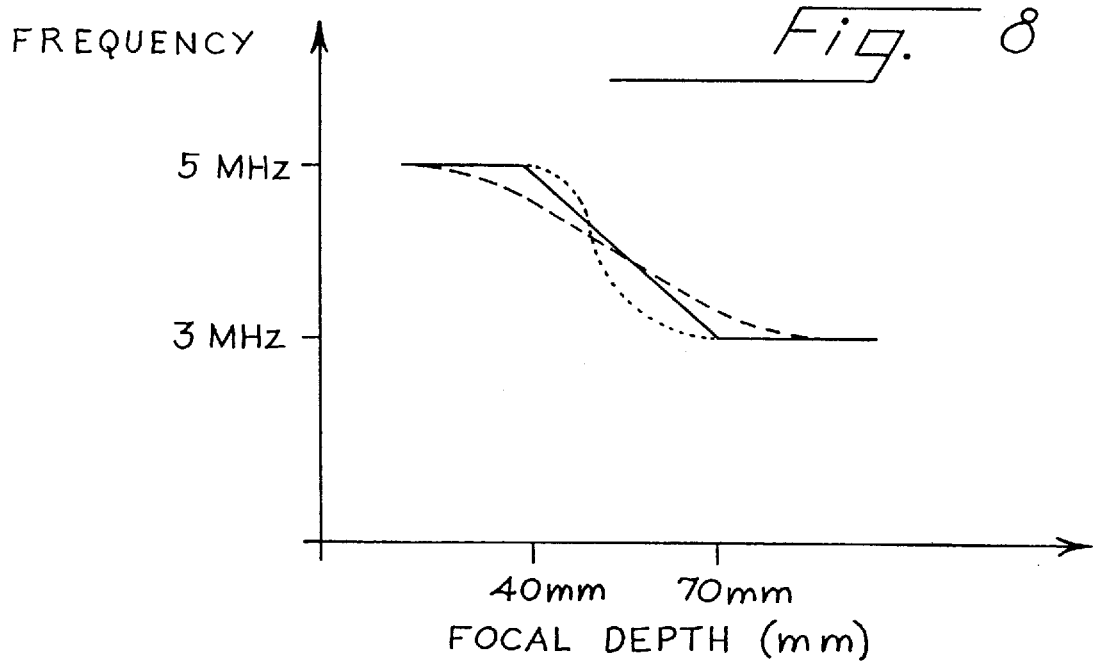
FIGS. 8 and 9 are graphs showing two alternative arrangements for allocating specific frequency components to specific focal depths in the system of FIG. 1.
Figure 9:
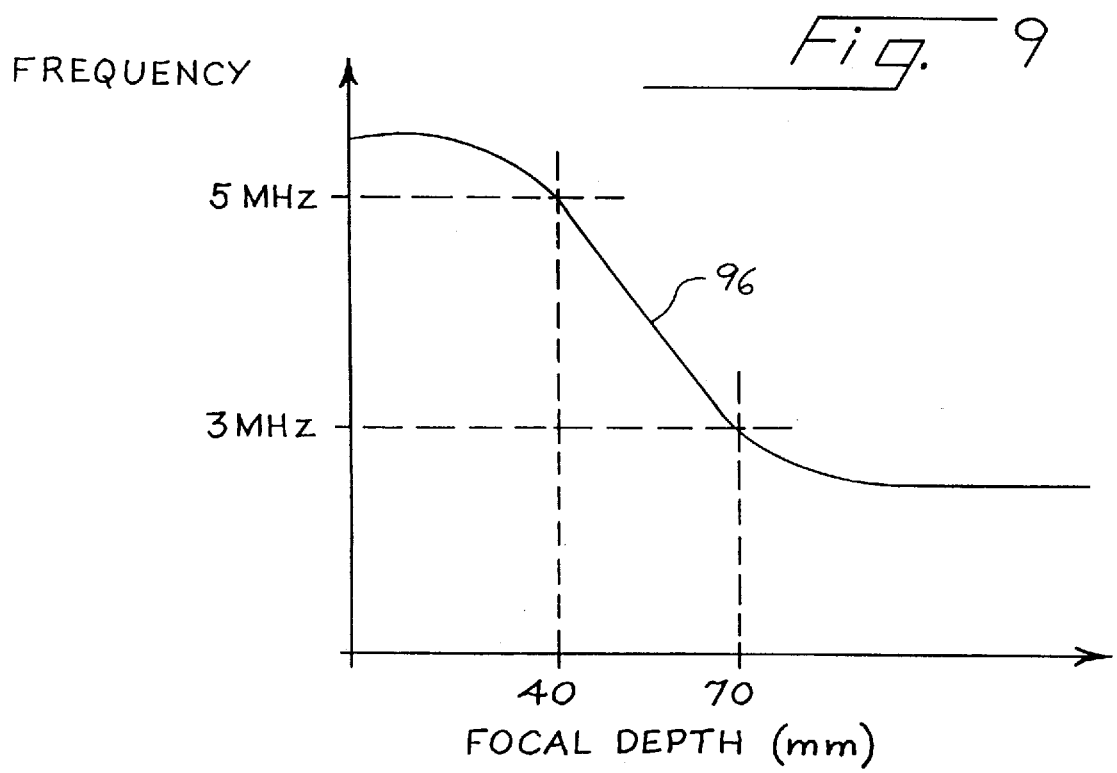

FIGS. 8 and 9 show two alternative functions that can be used to determine frequency as a function of focal depth for the color Doppler portion 92 of FIG. 7. In the function of FIG. 8, 5 MHz components are focused at depths below 40 mm., 3 MHz components are focused at depths greater than 70 mm., and there is a linear relationship between focal depth and frequency in the region between 40 and 70 mm. Alternative, non-linear relationships are shown in dotted lines. While the frequency for any particular focal depth is defined for all focal depths, the frequencies selected after demodulation and filtering represent only a fraction of those defined and transmitted. An advantage in terms of uniformity of performance may be gained by using a function of frequency versus focal depth that is relatively linear over the focal depth range of interest (40 to 70 mm in this example) in combination with a smoothly varying function of frequency versus focal depth outside this region. FIG. 9 shows a function 96 of this type.

With either the function of FIG. 8 or the function of FIG. 9, ultrasonic frequencies at or above 5 MHz are focused at ranges shorter than 40 mm and frequency components at or below 3 MHz are focused at ranges greater than 70 mm. In the region between 40 and 70 mm occupied by the color Doppler portion 92, progressively lower frequencies (below 5 MHz) are focused at progressively longer ranges, and a transmit beam having a substantially uniform width is provided in this region.

As explained above, this arrangement provides a more nearly uniform intensity of insonification, with resulting improvements in the uniformity of the signal to noise ratio and the reliability of multiple receive beams. As described in U.S. Pat. Nos. 5,555,534 and 5,608,690, multiple receive beams are preferably formed from each transmit beam. This has the advantage of providing improved or more uniform spatial resolution with no loss of temporal resolution, improved temporal resolution with no loss of spatial resolution, or a combination of improved temporal and spatial resolution. It is believed that when receive beams are offset by 0.5 degrees from the direction of the transmit beam, transmit waveforms generated as described above have the advantage of reducing image artifacts commonly encountered in the prior art as a result of a narrow focus of the transmit beam in the vicinity of the transmit focus and a broader width to the transmit beam elsewhere. This improvement in temporal resolution in Doppler imaging can be very important, since an ability to capture rapid blood jet dynamics is significant and typically is limited by the frame rate of the ultrasound imaging system.

Transmit waveforms generated as described above often result in a reduced axial resolution of the resulting image. However, such a reduction in axial resolution is often acceptable in color Doppler imaging, since there is a higher priority on a uniform, well-filled color region than on spatial resolution. That is, it is often preferable to have a well-filled color region than a region having nominally better axial resolution but which includes unfilled holes within the otherwise color-filled region.

Of course, many modifications and changes can be made to the preferred embodiment described above. For example, the calculation of the waveforms required for all combinations of user-selected color Doppler portions may be considered cumbersome. If so, it may be preferable to use approximations to allow the transmit waveforms to be calculated more quickly with reduced memory requirements. One method for providing such approximations is to use a parallel calculation approach in which the spectrum of the broadband excitation pulse is divided into a selected number of segments, such as four. Delay calculations for each of these spectral regions are made independently, and associated excitation waveforms are derived therefrom. Preferably, these excitation waveforms are Gaussian in form. Once these four sets of separately focused waveforms have been computed, they are summed as digital quantities prior to digitization and amplification. The transmit beamformer described in U.S. patent application Ser. No. 08/673,410, filed Jul. 15, 1996 and assigned to the assignee of the present invention, discloses hardware for performing this function in detail. In many cases it will be preferable to use a large number of discrete frequency bands and associated focal profiles, and a designer should balance the competing requirements for improved performance and reduced cost.

As another alternative, the frequency dependent focus methods described above may be combined with multizone techniques. That is, two or more transmit events may be steered in the same direction, but focused at different ranges (e.g. a first transmit event focused at 30–50 mm and a second transmit event focused at 50–70 mm).

Also, the methods described above may be used with both fundamental and harmonic imaging modes, and contrast agent (either linear or non-linear) may be added to the tissue or blood being imaged.

Also, many other types of components can be adapted for use with this invention. For example, any of the transmit beamformers described in Hossack U.S. Pat. No. 5,608,690 can be used. Similarly, any suitable receive beamformer including both analog and digital beamformers can be used. The processors 20, 22 and 26 can be formed as desired, using any suitable approach. For example, the color Doppler processor 22 can use frame-to-frame correlation techniques. The present invention is suitable for use with the widest variety of processors 20, 22, 26 as well as scan converters 26, memory 29 and display 30. For example, when the color Doppler processor 22 is adapted for use with tissue Doppler imaging, the clutter filter 72 and the low-pass filter 70 can be made less restrictive or even eliminated, as described in Arenson U.S. Pat. No. 5,285,788, to provide Doppler parameters (e.g. velocity, acceleration, energy) of slowly moving and/or substantially stationary tissue.

The foregoing detailed description has described only a few of the many forms that this invention can take. For this reason, it is intended that this description be regarded by way of example and not limitation. It is only the following claims, including all equivalents, that are intended to define the scope of this invention.

We claim:

1. A method for measuring Doppler ultrasound information comprising the following steps:
    (a) transmitting ultrasound energy with a plurality of transducers, each transducer responsive to a respective transmit waveform to produce a respective transducer waveform, each of at least a plurality of the transmit waveforms comprising at least first and second frequency components included in a single burst of energy, said first frequency components timed to cause corresponding first frequency components of the transducer waveforms to focus at a first depth, and said second frequency components timed to cause corresponding second frequency components of the transducer waveforms to focus at a second depth, less than the first depth;
    (b) generating beamformed receive signals in response to receive signals from the transducers; and
    (c) Doppler processing the beamformed receive signals.

2. The method of claim 1 wherein step (b) comprises the step of generating beamformed receive signals for multiple receive beams in response to receive signals associated with said single burst of energy.

3. The method of claim 1 wherein step (c) comprises the step of generating color flow information in response to the beamformed receive signals.

4. The method of claim 1 wherein step (c) comprises the step of processing the beamformed receive signals to form a color flow Doppler parameter.

5. The method of claim 4 wherein the Doppler parameter is indicative of flow velocity.

6. The method of claim 4 wherein the Doppler parameter is indicative of Doppler energy.

7. The method of claim 1 wherein step (c) comprises the step of processing the beamformed receive signals as a function of a detected Doppler frequency and an instantaneous transmitted center frequency, and wherein the instantaneous transmitted center frequency varies as a function of range.

8. The method of claim 1 wherein step (c) comprises the step of determining a Doppler velocity as a function of a range varying transmitted center frequency.

9. The method of claim 1 wherein step (c) comprises the step of generating Doppler parameters indicative of slowly moving tissue.

10. The method of claim 1 wherein step (c) comprises the step of generating Doppler parameters indicative of substantially stationary tissue.

11. An ultrasonic imaging system comprising:

a plurality of transducers, each transducer responsive to a respective transmit waveform to produce a respective transducer waveform;

a transmit beamformer comprising a transmit waveform generator that generates the transmit waveforms, each of at least a plurality of the transmit waveforms comprising at least first and second frequency components included in a single burst of energy, said first frequency components timed to cause corresponding first frequency components of the transducer waveforms to focus at a first depth, and said second frequency components timed to cause corresponding second frequency components of the transducer waveforms to focus at a second depth, less than the first depth;

a receive beamformer responsive to receive signals from the transducers to generate beamformed receive signals; and a Doppler processor responsive to the beamformed receive signals.

12. The invention of claim 11 wherein the first frequency component of one of the transmit waveforms is characterized by a lower frequency than the second frequency component of said transmit waveform.

13. The invention of claim 11 wherein the plurality of transducers includes all of the transducers of the transmit beamformer.

14. The invention of claim 11 wherein each transmit waveform comprises more than two frequency components, wherein progressively lower frequency components of the transmit waveforms are timed to cause corresponding progressively lower frequency components of the transducer waveforms to focus at progressively greater depths.

15. The invention of claim 11 wherein the first frequency components comprise components at 3 MHz, and wherein the second frequency components comprise components at 7 MHz.

16. The invention of claim 11 wherein the transducer waveforms are ultrasonic waveforms.

17. The invention of claim 11 wherein the first and second frequency components of each transmit waveform are included in a continuously varying portion of the respective transmit waveform.

18. The invention of claim 11 wherein the receive beamformer comprises a time-varying frequency filter to process receive signals from the transducers.

19. The invention of claim 18 wherein the receive beamformer comprises means for adjusting the filter in real time to emphasize a changing frequency of the arriving signals.

20. The invention of claim 11 wherein the transducers comprise a linear phased array.

21. The invention of claim 11 wherein the receive beamformer is operative to generate beamformed receive signals for multiple receive beams in response to receive signals associated with said single burst of energy.

22. The invention of claim 11 wherein the Doppler processor comprises a color flow Doppler processor.

23. The invention of claim 11 wherein the Doppler processor comprises means for processing the beamformed receive signals as a function of a detected Doppler frequency and an instantaneous transmitted center frequency, and wherein the instantaneous transmitted center frequency varies as a function of time.

24. The invention of claim 11 wherein the Doppler processor comprises means for determining a Doppler velocity as a function of a range-varying transmitted center frequency.

25. The invention of claim 11 wherein the Doppler processor is operative to generate Doppler parameters indicative of slowly moving tissue.

26. The invention of claim 11 wherein the Doppler processor is operative to generate Doppler parameters indicative of substantially stationary tissue.

* * * * *